United States Patent [19]

Decktor et al.

[11] Patent Number: 4,831,040

[45] Date of Patent: May 16, 1989

[54] METHOD OF PREVENTION AND TREATMENT OF PEPTIC ULCERS

[75] Inventors: Dennis L. Decktor, Dresher; Leo R. Fitzpatrick, Exton; Henry F. Campbell, North Wales, all of Pa.

[73] Assignee: Rorer Pharmaceutical Corporation, Fort Washington, Pa.

[21] Appl. No.: 150,808

[22] Filed: Feb. 1, 1988

[51] Int. Cl.$^4$ ............................................. A61K 31/44
[52] U.S. Cl. ........................................ 514/291; 514/293; 514/927
[58] Field of Search .......................... 514/291, 293, 927

[56] References Cited

U.S. PATENT DOCUMENTS 4,522,947 6/1985 Musser et al. ...................... 514/293

Primary Examiner—Frederick E. Waddell

[57] ABSTRACT

Disclosed is a method for prophylactic and therapeutic treatment of peptic ulcers which comprises the administration of a pharmaceutical composition containing a compound of the formula

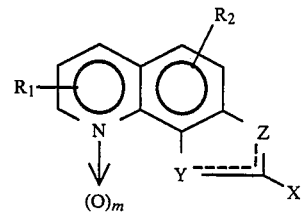

or a pharmaceutically acceptable salt thereon, wherein $R_1$ and $R_2$ are independently hydrogen, lower alkyl, halo, trifluoromethyl, amino, lower alkyl amino, lower acylamino, cyano, aryl, aryl/lower alkylene, nitro, lower alkynyl, lower alkenyl, lower alkyl sulfinyl, lower alkyl sulfonyl, lower alkoxycarbonyl, carboxyl, lower alkoxy, lower alkanoyl, or lower alkenoyl, Y is oxygen, sulfur, nitrogen or $R_3N$ wherein $R_3$ is hydrogen, lower alkyl, alkenyl, alkynyl, aryl, aralkyl, acyl, aminolakyl, or carboxyalkyl, Z is oxygen, sulfur or nitrogen, X is cyano, carbalkoxyl, carboxyl, formuloximino, tetrazolyl, carbalkoxyalky or caboxyalkyl, and m is 0 or 1, in admixture or in association with a pharmaceutically acceptable carrier.

3 Claims, No Drawings

METHOD OF PREVENTION AND TREATMENT OF PEPTIC ULCERS

BACKGROUND OF THE INVENTION

1. Field of the Invention

Chronic gastric and duodenal ulcers, known as peptic ulcers, are caused by the action of the gastric juice on the mucous membrane of the esophagus, stomach and duodenum. The present invention relates to a method for the prevention and treatment of such ulcers utilizing compounds and compositions which inhibit mast cell degranulation and histamine release.

2. Description of the Prior Art

The prior art employs a variety of treatments for peptic ulcers, including the use of diet, surgery and therapeutic agents. Among the various treatments proposed, therapeutic agents that exert antagonism to histamine $H_2$-receptors, to suppress gastric secretion and provide shielding to the mucous membrane, represent considerable research effort examples of which follow.

U.S. Pat. No. 4,673,747 issued to Nohara et al. discloses aminoalkylphenoxy derivatives that exert antagonism against Histamine $H_2$-receptors, suppressing gastric secretion and hence effective for the treat- of digestive ulcers.

U.S. Pat. No. 4,507,485 is issued to Monkovic et al. pertains to 3,4-disubstituted-1,2,5-oxadiazoles having Histamine $H_2$-receptor antagonist activity.

U.S. Pat. No. 5,529,602 issued to Wada et al. teaches a method for the treatment of prophylaxis of peptic ulcer diseases or gastritis.

U.S. Pat. No. 4,678,794 issued to R. Crossley relates to the anti-ulcer agent, N-pyridyl-substituted pyridine-2-carboxamide-1-oxides.

U.S. Pat. No. 4,590,299 issued to LaMattina et al. discloses 2-guanidino-4-heteroaryl-thiazles for the treatment of gastric hyperacidity and peptic ulcers.

SUMMARY OF THE INVENTION

In accordance with the present invention, there is provided a method for the prevention and treatment of peptic ulcers which comprises: the administration to a patient in need of such prevention or treatment an effective amount of a compound of formula I:

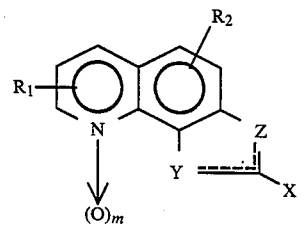

or a pharmaceutically acceptable salt thereon, wherein $R_1$ and $R_2$ are independently hydrogen, lower alkyl, halo, trifluoromethyl, amino, lower alkyl amino, lower acylamino, cyano, aryl, aryl/lower alkylene, nitro, lower alkynyl, lower alkenyl, lower alkyl sulfinyl, lower alkyl sulfonyl, lower alkoxycarbonyl, carboxyl, lower alkoxy, lower alkanoyl, or lower alkenoyl, Y is oxygen, sulfur, nitrogen or $R_3N$ wherein $R_3$ is hydrogen, lower alkyl, alkenyl, alkynyl, aryl, aralkyl, acyl, aminolakyl, or carboxyalkyl, Z is oxygen, sulfur or nitrogen, X is cyano, carbalkoxy, carboxyl, formyloximino, tetrazolyl, carbalkoxyalkyl or carboxyalkyl, and m is 0 or 1, in admixture or in association with a pharmaceutically acceptable carrier.

DETAILED DESCRIPTION OF THE INVENTION

It has been surprisingly found that compounds disclosed in U.S. Pat. No. 4,698,346 (which is incorporated herein by reference) as antiallergic agents possess valuable pharmaceutical properties for the prevention and treatment of peptic ulcers.

The invention, in its broad aspects, includes the use of derivatives of quinoline, and corresponding benzodiazine compounds of formula I. Within this broad group, because of their properties, certain subgroups are preferred over others.

In the preferred compounds, Z is nitrogen, $R_3$ is hydrogen, alkyl aminoalkyl or carboxyalkyl of from about 1–5 carbon atoms and m is 0.

It is preferable that when Y is oxygen, Z be nitrogen; that when Z is sulfur, Y be nitrogen; and that when Z is nitrogen, Y be oxygen, sulfur or $R_3N$.

In the most preferred compounds, Z is nitrogen and Y is oxygen. In slightly less preferred compounds, Z is oxygen and Y is nitrogen.

When X includes an alkyl group, it is preferred that the alkyl contain 1 to 5 carbon atoms.

The preferred X groups are those including carboxy groups and, more preferably, carboxy groups directly attached to the ring. These groups include those having the general formula

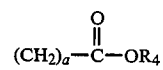

wherein a is 0 or 1, preferably 0, and $R_4$ is H or a lower alkyl group, preferably having 1–12 carbon atoms, more preferably having 1–5 carbon atoms, or an alkyl group substituted with an alkoxy or amino group. $R_4$ can also be a metal or organic cation, preferably an alkali metal cation.

The compounds in which X is formyloximino or cyano are preferred as intermediates in a process for making the preferred carboxy compounds of this invention.

More than one $R_1$ or $R_2$ substituent can be on the respective rings. It is preferred that $R_1$ be hydrogen, $C_1$–$C_5$ alkyl, particularly methyl or ethyl, halo, particularly chlorine or bromine, trifluoromethyl or benzyl. It is most preferred that $R_1$ be hydrogen. It is preferred that $R_2$ be hydrogen, $C_1$–$C_5$ alkyl, halo, particularly chloro, trifluoromethyl, nitro, $C_1$–$C_5$ alkylamino or acylamino. It is most preferred that $R_2$ be at the 5 position.

The preferred compounds include those in which the quinoline ring structure is present. The present invention also embraces the corresponding benzodiazines, e.g., 1,4-benzodiazines of the formula:

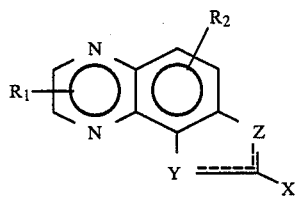

as well as the 1,2- and 1,3-benzodiazines. The invention is illustrated by way of the preferred quinoline compounds but it is within the skill of the art to extend the illustration to benzodiazines.

The quinoline compounds of the present invention can be prepared, in general, by reaction of the following compounds under condensation conditions to form the desired heterocyclic ring:

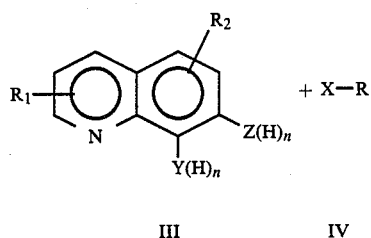

wherein
$R_1$, X, Y, Z and $R_2$ are as hereinbefore defined;
n=1 except when Y or Z is N when n=2; and
R=a di- or trifunctional group capable of condensing with $Y(H)_n$ and $Z(H)_n$ to form the indicated heterocyclic ring, e.g., trihalomethyl, trialkoxymethyl, or formuyloximino.

A typical procedure for preparing the quinoline compounds where Z is N and Y is O, S or $R_3$ follows:

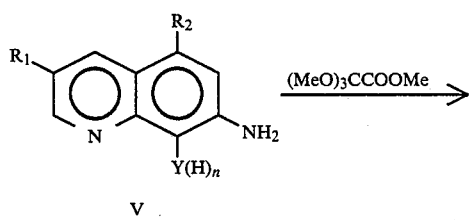

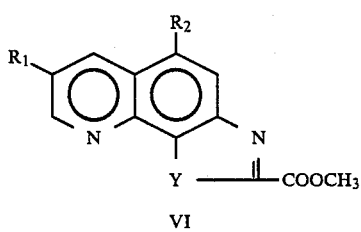

In this illustration, X is carbomethoxy but may be any of the groups representative of X.

A particularly preferred procedure for production of the compounds, especially the preferred compounds in which X is a carboxy group attached to the ring involves condensation of

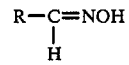

with a selected 7-amino-8-hydroxyquinoline to form the corresponding 2-formyloximino-1,3-oxazolo[4,5-h]-quinoline from which the corresponding cyano compound can be prepared by dehydration of the oximino compound and the cyano compound then converted to carboxy or carbalkoxy by known hydrolysis or alcoholysis reaction. The condensation with the oxime is usually carried out in a reaction solvent, preferably but not essentially, in the presence of base catalyst, such as alkali metal salts of organic carboxylic acids such as salts of acetic acid, e.g., sodium acetate. The use of temperatures higher than room temperature merely shortens the requisite reaction time. Temperatures from 0° C. up to 150° C. can be used.

Compounds in which m=1, i.e., the N-oxides, can be formed by reaction of corresponding compounds in which m=0 with peroxide or equivalent peracids. Thus, reaction is effected with hydrogen peroxide, perbenzoic acid, peracetic acid, and other peroxides commonly used for this purpose. Generally, the N-oxide formation is carried out at room temperature or lower, to as low as 0° C., for example. For convenience, the starting compound may be dissolved in a suitable reaction solvent. Although only equivalent amounts of peroxide are required, usually excess is used to assure complete reaction.

Solvents employed in the present preparative processes may be amy of those commonly used in organic preparation such as dioxane, tetrahydrofuran, dimethyl acetamide, dimethyl formamide and similar solvents. Solvents are not always necessary, however, since the condensation of compounds of formula III with those of formula IV can be carried out without solvent by mere mixing of the reactants, preferably with use of reaction temperatures above room temperature, up to above 150° C. and preferably from about 50° C. to about 125° C.

The compounds used in the invention will be more fully illustrated in the examples which follow. These examples are given by way of illustration and are not considered as limiting.

EXAMPLE 1

A. 5-Chloro-7-nitro-8-hydroxyquinoline

To a solution of 5-chloro-8-hydroxyquinoline (90.0 g, 0.5 mol) 9n sulfuric acid (500 ml) at 0° C. was added 90% nitric acid (0.6 mol) at such a rate that the temperature did not exceed 2° C. The clear solution was stirred for one hour at 0° C., and then allowed to slowly warm to room temperature. The mixture was poured into ice (2 liter) and stirred overnight. The yellow precipitate was filtered, washed with water and dried. The yellow cake was crystallized from methylethylketone giving 85.0 g (76% yield) of solid. M.P. 192° C.–194° C.

B. 5-Chloro-y-amino-8-hydroxyquinoline

To a suspension of 5-chloro-7-nitro-8-hydroxyquinoline (85.0° C. g, 0.38 mol) in a 1:1 mixture of methanol and water (2.5 liter) was added sodium dithionite (340 g, 2.0 mol). The reaction which is slightly exothermic was stirred overnight under nitrogen. The yellow solid was filtered, washed with water and crystallized from ethanol giving 52 g (70% yield) of solid. M.P. 162° C. to 164° C.

C.
2-Carbomethoxy-5-chloro-1,3-oxazolo-[4,5-h]quinoline

A mixture of 5-chloro-7-amino-8-hydroxyquinoline (6 g, 30.8 mol) and methyl trimethoxyacetate (16.3 g, 123.2 mol) was heafted at 100° C. overnight. The reaction was cooled in an ice bath and filtered. The precipitate was dissolved in acetone (250 ml). The resulting solution was treated with charcoal at reflux, filtered through a pad of silica gel and celite and partially concentrated. Crystals formed which were filtered and dried giving 4.1 g (51% yield) of solid. M.P. 217° C. to 218° C.

EXAMPLE 2
A.
2-Formyloximino-5-chloro-1,3-oxazolo-[4,5h]quinoline

A solution of chloral hydrate (1.7 g, 10 mmol) in water (10 ml) containing an equivalent amount of hydroxylamine to form the oxime was heated at 60° C. for three hours. Then a solution of 5-chloro-7-amino-8-hydroxyquinoline (0.9 g, 4.6 mmol) in DMF (10 ml) was added. To this mixture was added sodium acetate (3.2 g, 40 mmol) portionwise over a two hour period. The reaction was heated at 60° C. for an additional hour. The solvent was removed in vacuo. The remaining material was triturated with water, filtered and dried. The solid was dissolved in acetone, treated with charcoal and filtered through a pad of celite and silica gel. The solvent was removed given the desired product. M.P. 220° C.-dec.

B. 2-Cyano-5-chloro-1,3-oxazolo-[4,5-h]quinoline

A suspension of 2-formyloximino-5-chloro-1,3-oxazolo[4,5-h]quinoline (0.7 g 2.8 mmol) in toluene (300 ml) was treated with thionyl chloride (0.3 ml) and refluxed for one hour. The reaction was filtered, and concentrated. The remaining material was dissolved in acetone and filtered through a pad of silica gel and celite. The solvent was removed giving the desired product. M.P. 214° C. to 215° C.

C.
2-Carboxymethoxy-5-chloro-1,3-oxazolo-[4,5-h]quinoline

A solution of 5 g of 2-cyano-5-chloro-1,3-oxazolo-[4,5-h]quinoline in 100 ml of methanol was cooled to 0° C. and dry HCl was bubbled through the solution for 1 hour. The solution was then maintained at 0° C. for 24 hours, then allowed to warm up to room temperature. The solvent was removed in vacuo and the residue was dissolved in acetone and filtered through a pad of silica gel and celite. The solvent was removed to give the desired product. M.P. 214° C. to 215° C.

EXAMPLES 3–4

In like manner as above using 7-amino-5-chloro-8-hydroxyquinoline and the appropriate ortho esters or imidates, the following compounds were prepared:
3. 5-chloro-1,3-oxazolo-[4,5-h]quinoline 2-acetic acid, ethyl ester. M.P. 118° to 121° C.
4. 2-carboethoxy-5-chloro-1,3-oxazolo-[4,5-h]quinoline. M.P. 150° C. to 152° C.

EXAMPLES 5–13

The following compounds can be made using the above procedure and the appropriate aminoquinolines and imidates or ortho esters:
5. 8-methyl-2-carbomethoxy-1,3-oxazolo-[4,5-h]quinoline.
6. 5-(N,N-dimethylamino)-2-carbomethoxy-1,3-oxazolo-[4,5-h]quinoline.
7. 2-carboethoxy-1,3-oxazolo-[4,5-h]quinoline.
8. 8-trifluoromethyl-2-carbomethoxy-1,3-oxazolo-[4,5-h]quinoline.
9. 5-cyano-1,3-oxazolo-[4,5-h]quinoline-2-propanoic acid, methyl ester.
10. 5-bromo-2-(5-tetrazolyl)1,3-oxazolo-[4,5-h]quinoline.
11. 5-methyl-2-carbopentoxy-1,3-oxazolo-[4,5-h]quinoline.
12. 2-carboxy-5-trifluoromethyl-1,3-oxazolo-[4,5h]quinoline ethoxyethyl ester.
13. 2-carboxy-5-nitro-1,3-oxazolo-[4,5-h]quinoline diethylaminoethyl ester.

EXAMPLE 14
5-chloro-1,3-oxazolo-[4,5-h]quinoline-2-carboxylate sodium salt A suspension of 2-carboethoxy-5-chloro-1,3-oxazolo[4,5-h]quinoline (1.5 g) in water (100 ml) was treated with 16.3 ml of 1N NaOH. After 10 minutes, the aqueous phase was extracted with chloroform. The aqueous phase was then treated with saturated ammonium chloride causing a white precipitate to form. The filtrate was concentrated in vacuo giving 0.9 g of solid, M.P. 212° C. to 216° C. which was suspended in water (50 ml), treated with one equivalent of sodium hydroxide, and lyophilized to give 0.9 g of product. M.P. 200° C.-dec.

EXAMPLE 15

In like manner as above using the appropriate base, the following salt was prepared:
5-chloro-1,3-oxazolo-[4,5-h]quinoline-2-carboxylate, tris(hydroxymethyl)amino methane salt. M.P. 90° C. -dec.

EXAMPLE 16
2-(5-tetrazolyl)-5-chloro-1,3-oxazolo-[4,5-h]quinoline

A mixture of 5 g of 2-cyano-5-chloro-1,3-oxazolo-[4,5-h]quinoline and 1.0 g of sodium azide and 2 g of ammonium chloride in 100 ml of DMF are heated for 3 hours at 120° C. The reaction mixture is poured into water acidified with dilute HCl, and the product is filtered and recrystallized.

EXAMPLE 17

Other compounds within the current invention which can be prepared include the following in which $R_1$, $R_2$ and X can be as disclosed above.
(A) Oxazolo-[5,4-h]quinolines as, for example, 2-carbomethxy-1,3-oxazolo-[5,4-h]quinoline.
(B) Imidazo-[4,5-h]quinolines as, for example, 2-carbomethoxy-1,3-imidazo-[4,5-h]quinoline.
(C) Thiazolo-[4,5-h]quinolines as, for example, 2-carbomethoxy-1,3-thiazolo-[4,5-h]quinoline, and 2-carbomethoxy-1,3-thiazolo-[4,5-h]quinoline-N-oxide.
(D) Thiazolo-[5,4-]quinolines as, for example, 2-carbomethoxy-1,3-thiazolo-[5,4-h]quinoline.

(E) Oxazolo-[4,5-h]quinolines as, for example, 2-carbomethoxy-5-chloro-1,3-oxazolo-[4,5-h]quinoline-N-oxide; and 2-formyloximino-5-chloro-1,3-oxazolo-[4,5-h]quinoline.

The activity of the compounds of the present invention were determined by studies being described hereunder.

I. ULCER HEALING PROTOCOLS

(A) Acetic Acid-induced Gastric Ulcers

Gastric ulcers were produced according to the method described by Takagi, et al. (Jap. J. Pharmacol. 19, 418–426, 1969), by ijecting 0.05 ml of 10% acetic acid into the subserosal layer in the glandular protion of the anterior stomach wall. Rats were then maintained on a dietary and treatment regimen, as described by Ito, et al. (Jap. Pharmacol. 41, 260, 1986). Animals were fed twice daily, for one hour (7:30–8:30 A.M.) and (3:00–4.00 P.M.). Compounds or vehicle were administered orally 30 minutes after these feeding periods. The compound of Example 2C (2-carbomethoxy-5-chloro-1,3-oxazolo-[4,5-h]quinoline), hereinafter compound A and Ranitidine were given at doses of 50 mg/kg, therefore rats received a total daily dose of 100 mg/kg. This type of experimental regimen was reported by Ito, et al. (supra) to: (1) delay the healing of acetic acid induced gastric ulcers; and (2) decrease the measured ulcer index in conjunction with $H_2$ antagonist treatment (i.e. Cimetidine).

Results are shown in Table I.

TABLE I
ACETIC ACID INDUCED GASTRIC ULCERS
(Healing Study of Compound A vs. Ranitidine)

| Treatment Group | Ulcer Index ($mm^2$) | | |
|---|---|---|---|
| | Day 5 | Day 10 | Day 15 |
| Control | 35.2 ± 8.6 | 17.5 ± 6.2 | 6.7 ± 2.2 |
| Ranitidine | 14.5[1] ± 3.3 | 8.5 ± 1.6 | 5.3 ± 1.7 |
| A | 13.5[1] ± 3.0 | 8.2 ± 1.6 | 1.6[2] ± 0.3 |

Compounds were administered orally at a dose of 50 mg/kg, b.i.d. N = 6–12 per treatment group.
[1] $P < 0.05$ or
[2] $P < 0.01$ vs. control.
The ulcer index is the mean ulcer score of each group.

(B) Mepirizol-induced Duodenal Ulcers

Duodenal ulcers were produced according to the method described by Okabe, et al. (Dig. Dis. & Sci. Vol. 27, No. 3, 1982), by administering p.o. mepirizole (200 mg/kg suspended in 1% carboxymethylcellulose solution) to fasted male Sprague-Dawley strain rats 180–200 g. 24 hours after mepirizole administration 20 randomly chosen rats were killed and examined to allow verification of ulcer formation. Three treatment groups subsequently received daily doses of a vehicle control (0.5% methylcellulose, 10 ml/kg, compound A (25 mg/kg) or ranitidine (25 mg/kg). After 2, 4, or 10 days of treatment, rats were killed and their duodenum examined. The severity of the remaining lesion was assessed in accordance to the following scale:
0: No lesion
0.5: Lesion diameter—1 mm
1.0: Lesion diameter 2–3 mm
1.5: Lesion diameter 4–5 mm or 5×1.5 mm
2.0: Lesion 6×2.5 mm
2.5: Lesion 7×3 mm
3.0: Full perforation 3–4 mm diameter
3.5: Full perforation 5–6 mm diameter
4.0: Full perforation 6–7×2.5 mm
4.5: Full perforation 8–9×3 mm
5.0: Full perforation 10×3 mm The ulcer index presented in the mean ulcer score of each group.

Results are shown in Table II.

TABLE II
MEPIRIZOLE INDUCED DUODENAL ULCERS
(Healing Study of Compound A vs. Ranitidine)

| Treatment Group | Ulcer Index ($mm^2$) | | |
|---|---|---|---|
| | Day 2 | Day 4 | Day 10 |
| Control | 3.0 ± 0.52 | 1.5 ± 0.48 | 0.94 ± 0.4 |
| Ranitidine | 1.6[1] ± 0.41 | 1.0 ± 0.41 | 0.38 ± 0.2 |
| A | 1.4[1] ± 0.39 | 0.7 ± 0.27 | 0.25 ± 0.16 |

Compounds were administered orally at a dose of 25 mg/kg once per day. N = 8 per treatment group.
[1] $< 0.05$ vs control.

II. ULCER PROTECTION MODELS

(A) Acid-Independent (1) Ethanol-induced

Twenty-eight male Sprague-Dawley rats were fasted 24 hours but allowed free access to water. Rats were randomly selected into four groups of seven (one control and three experimental groups). Rats in the control group received vehicle (0.5% methylcellulose) at a dose volume of 10 ml/kg. The experimental groups received the test compounds in the dosage amounts shown in Table III. 1.0 ml of absolute ethanol was orally administered to each rat thirty minutes post-drug. Animals were killed after 1 hour. The Stomachs were removed, opened along the greater curvature, gently rinsed with water and kept moist until macroscopic examination.

Macroscopic examination of the rat stomach was performed. This included the counting of alcohol-induced red lesion bands that develop in the corpus, the main acid and pepsin secreting portion of the stomach. The macroscopic lesion score of the gastric mucosa was determined under a SMX 10 Nikon steromicroscope at 2.5× magnification by counting the total number of lesions found on the mucosa and determining the severity of damage using the following scale on the largest lesion found.
a. 1: punctate
b. 2: <0.5 mm×1–5 mm
c. 3: <0.5 mm×6–10 mm
d. 4: 0.5–1.0 mm×1–5 mm
e. 5: 0.5–1.0 mm×6–10 mm
f. 6: >1.0 mm or >10 mm
g. 0: no lesions Data Analysis for Macroscopic Study:

The ulcer index is the sum of the number of gastric lesions counted plus the severity score, the mean ulcer index (+/−S.E.M.) is calculated for each experimental and control group.

The percent inhibition of the ulcer index is calculated as follows:

$$\% \text{ Inhibition} = \frac{\text{Mean Value Control} - \text{Mean Value Experimental}}{\text{Mean Value Control}} \times 100$$

Results are shown in Table III.

TABLE III

| | Ethanol-induced Ulcer Protection | |
|---|---|---|
| Compound | Dose mg/kg | Inhibition % |
| Ranitidine | 0.5 | 50 |
| A | 0.85 | 50 |
| B | 25 | 87 |
| C | 25 | 67 | wherein and hereinafter:
B = 5,6,7,8-tetrahydronaphthoxazole-2-carboxylate sodium salt; and
C = ethoxyethyl 5-chlorobenzoxazole-2-carboxylate.

(2) Acid-induced

Male Sprague-Dawley rats were fasted 24 hours (water ad libitum) prior to the experiment. Rats were randomly selected into test groups of seven, with one group serving as control and receiving the vehicle. The test compounds and controls were administered orally at a dose volume shown in Table IV. Thirty minutes post-treatment, rats were orally administered 1.0 ml of 0.6N HCl. Animals were sacrificed after 1 hour. The stomachs were removed, opened along the greater curvature, gently rinsed and graded for number and severity of gastric lesions. Grading was based on an Ulcer Index which is the sum of the mean number of gastric lesions and the mean lesion severity score. Lesion severity was obtained by determination of the size of the largest lesion as follows:

a. 1: punctate=1
b. 2: <0.5 mm×1-5 mm=2
c. 3: <0.5 mm×6-10 mm=3
d. 4: 0.5-1.0 mm×1-5 mm=4
e. 5: 0.5-1.0 mm×6-10 mm=5
f. 6: >1.0 mm or >10 mm=6
g. 0: no lesions=0

Percent inhibition was calculated as shown under the Ethanol-induced protocol, supra.

Results are shown in Table IV.

TABLE IV

| | Acid-Induced Ulcer Protection | |
|---|---|---|
| Compound | Dose mg/kg | Inhibition % |
| A | 25 | 80 |
| B | 25 | 42 |
| C | 25 | 41 |

(B) Acid-dependent (1) Indomethacin- and
(2) Aspirin-induced

This method is a modification of "Interaction of Salicylates and other Non-steroidal Anti-inflammatory Agents in Rats as shown by Gastro-ulcerogenic and Anti-inflammatory Activities, and Plasma Concentrations" by Corell, T., Acta. Pharmacology et. Toxicology, 45, 225-231 (1979).

Male Sprague-Dawley rats 140-170 g were housed according to standard animal husbandry procedures. The rats were fasted twenty-four hours prior to testing. On the test day, rats were divided into groups of 5 or 10, with one group serving as controls and receiving vehicle (distilled water or a 0.1%.Tween 80 solution). The test compound, using logarithmic doses, was administered at a dose volume of 10 ml/kg. Thirty minutes post-drug, one set of rats were orally administered (10 ml/kg) idomethacin and another set of rats were administered (10 ml/kg) aspirin suspended in 0.1% Tween 80 at a dose of 150.0 mg/kg and 20.0 mg/kg, respectively.

Four hours following indomethacin administration (five hours after aspirin administration) animals were sacrificed via cervical dislocation; stomachs were removed, opened along the greater curvature, and gently rinsed and examined for lesion with a 10× magnifying glass; the following scale was employed:

| Grade | Description |
|---|---|
| 0 | No lesions |
| 1 | 5 lesions, all < 2 mm |
| 2 | 5 lesions, at least 1 > 2 mm |
| 3 | 5-10 lesions, all < 2 mm |
| 4 | 5-10 lesions, at least 1 > 2 mm |
| 5 | 10 lesions, all < 2 mm |
| 6 | 10 lesions, at least 1 > 2 mm |
| 7 | Perforation |

The average ulcer severity ($\pm$S.E.) for each group of animals was calculated. The percent inhibition for each test compound was calculated as shown under the Ethanol-induced protocol, supra.

Results are shown in Table V

TABLE V

| | Acid-dependent Ulcer Protection | | | |
|---|---|---|---|---|
| | Indomethacin | | Aspirin | |
| Compound | Dose mg/kg | Inhibition % | Dose mg/kg | Inhibition % |
| Ranitidine | 4.4 | $ED_{50}$ | 4.9 | $ED_{50}$ |
| A | 50 | IA | 50 | IA |

(C) Restraint-stress-induced Ulcers

This method is based on "A Study of the Factors Involved in the Production of Gastric Ulcers by the Restraint Technique" by Brodie, et al. Gastroenterolgy, 38, 353-360 (1960).

Male Holtzman rats 90-110 g were fasted 24 hours prior to the experiment. On the test day, rats were divided into groups of 8 to 10, with one group serving as controls and receiving vehicle (distilled water or 0.1% Tween 80 solution). Test compounds were administered at a dose volume of 5 or 10 ml/kg. 15 minutes post-drug, the animals were placed in a piece of galvanized steel window screen of appropriate size. The screen was molded around the animal and held in place with wire staples. The wire was tightened around the animal so that it could not move. The animals were restrained for a 6 or 24 hour period (separated by at least 15 cm).

At the end of the restraint period the animal was removed from the screen and sacrificed by cervical dislocation. Each stomach was examined and the number of ulcers per stomach was recorded.

The average number of ulcers ($\pm$S.E.) for each group of animals was calculted. The % inhibition for each test compound was calculated as shown under the Ethanol-induced protocol, supra.

Consistency in the degree of tightness of restraint is very important and difficult to achieve. A somewhat loosely restrained rat will not get ulcers. Thus, control groups were always necessary. Experiments in which control groups possessed less than 90% ulcer incidence were discarded.

Results are shown in Table VI.

TABLE VI

| | Restraint-stress Ulcer | |
|---|---|---|
| Compound | Dose mg/kg | Inhibition % |
| A | 6.2 | 50 |
| B | 25 | IA |
| C | 25 | 28 |

III. Pylorus-Ligated Rat-Inhibition of Gastric Secretion

The method employed was a modification of that reported by Shay, et al. Gastroenterology, 26, 906-913 (1954). Male Sprague-Dawley rats, weighing between 140-160 g, were fasted twenty-four hours prior to the study (water ad lib.). The compounds are given orally, 30 minutes prior to pyloric ligation using logarithmic doses, and are dissolved in distilled water or suspended in 0.5% methylcellulose or 0.1% Tween 80.

Under ether anesthesia, a midline incision was made extending from the xiphoid for about 2 cm. Using a small hemostat, a pyloric ligature was placed around the pyloric sphincter. The incision was closed with wound clips, cleansed of blood with gauze and sealed with a plasticbandage (flexible colodion).

Four hours subsequent to surgery the animals were sacrificed (sodium pentobarbital) by cervical dislocation, the abdomen was opened, the esophagus clamped off, and the stomach removed. The gastric contents were emptied into graduated centrifuge tubes, spun for 15 minutes at 2400 rpm and all samples having a volume of solids over 0.6 ml were discarded. The gastric contents are assayed for acid concentration and total acid output.

For each animal the total secreted volume (corrected for solids), concentration, and total acid output was recorded. For each group the mean ±SEM for each of these parameters was calculated. The percentage inhibition was calculated as shown under the Ethanol-induced protocol, supra.

Results are shown in Table VII

TABLE VII

| Pylorus-Ligated Rat-Inhibition of Gastric Secretion | | |
|---|---|---|
| Compound | Dose mg/kg | Inhibition % |
| A | 25 i.d. | 0 |
| A | 50 i.d. | 0 |
| A | 100 i.d. | 0 |

As above-illustrated, compounds of the present invention have activity in both the prevention and treatment of peptic ulcers. The compounds and compositions may be administered to a patient in need of such prevention or treatment by conventional routes of administration including orally and parenterally. In general, the compounds will be administered orally at doses between about 0.2 and 25 mg/kg body weight per day, preferably from about 0.5 to 5 mg/kg per day. The physician will determine the required dosage depending upon the condition of the patient being treated. It is preferred that the compounds be administered in combination with a pharmaceutically acceptable carrier. A wide variety of pharmaceutical forms may be employed, such as tablet, ccapsule, powder, troche or lozenge, syrup, emulsion, aqueous or non-aqueous liquid suspension. If desired, the composition may contain additional ingredients, such as flavorings, binders, excipients and the like.

What is claimed is:

1. A method for treating peptic ulcer in a patient which comprises the administration to said patient a therapeutically effective amount of a compound of the formula

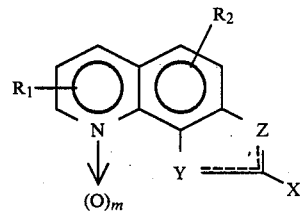

or a pharmaceutically acceptable salt thereof, wherein
$R_1$ and $R_2$ are independently hydrogen, lower alkyl, halo, trifluoromethyl, amino, lower alkyl amino, lower acylamino, cyano, aryl, aryl/loer alkylene, nitro, lower alkynyl, lower alkenyl, lower alkyl sulfinyl, lower alkyl sulfonyl, lower alkoxycarbonyl, carboxyl, lower alkoxy, lower alkanoyl, or lower alkenoyl;
Y is oxygen, sulfur, nitrogen or $R_3N$ wherein $R_3$ is hydrogen, lower alkyl, alkenyl, alkynyl, aryl, aralkyl, acyl, aminoalkyl, or carboxyalkyl;
Z is oxygen, sulfur or nitrogen;
X is cyano, carbalkoxyl, carboxyl, formyloximino, tetrazolyl, carbalkoxyalkyl or carboxyalkyl, and m is 0 or 1, in admixture with a pharmaceutically acceptable carrier.

2. The method of claim 1 wherein
$R_1$ and $R_2$ are independently hydrogen, $C_1$–$C_5$ alkyl, halo, trifluoromethyl, amino, $C_1$–$C_5$ alkyl amino, cyano, $C_1$–$C_5$ alkenyl, nitro, $C_1$–$C_5$ alkyl sulfinyl, $C_1$–$C_5$ alkyl sulfonyl, $C_1$–$C_5$ alkoxy-carbonyl, carboxyl, $C_1$–$C_5$ alkoxy, $C_1$–$C_5$ alkanoyl, or $C_1$–$C_5$ alkenoyl;
m is 0 or 1; and
X is cyano, formyloximino, tetrazolyl, carbalkoxy $C_1$–$C_5$ alkyl, carboxy $C_1$–$C_5$ alkyl, or $COOR_4$ in which the $R_4$ group is hydrogen, $C_1$–$C_5$ alkyl or a $C_1$–$C_5$ alkyl substituted by a $C_1$–$C_5$ alkoxy or amino group.

3. A method for treating peptic ulcer in a patient which comprises the administration to said patient a therapeutically effective amount of a compound selected from the group consisting of carbomethoxy-5-chloro-1,3-oxazolo-[4,5-h]quinoline; 5,6,7,8-tetrahydronaphthoxazole-2-carboxylate; ethoxyethyl 5-chlorobenzoxazole-2-carboxylate and a pharmaceutically acceptable salt thereof in association with a pharmaceutically acceptable carrier.

* * * * *